(12) United States Patent
Basu et al.

(10) Patent No.: US 11,918,751 B2
(45) Date of Patent: Mar. 5, 2024

(54) CATHETER WITH VAPOR DEPOSITED FEATURES ON TIP

(71) Applicant: Biosense Webster (Israel) Ltd., Yokneam (IL)

(72) Inventors: Shubhayu Basu, Anaheim, CA (US); Dustin R. Tobey, San Dimas, CA (US); Pieter E. Van Niekerk, Monrovia, CA (US); Cesar Fuentes-Ortega, Pasadena, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 364 days.

(21) Appl. No.: 17/084,776

(22) Filed: Oct. 30, 2020

(65) Prior Publication Data

US 2021/0137589 A1     May 13, 2021

Related U.S. Application Data

(60) Provisional application No. 62/934,077, filed on Nov. 12, 2019.

(51) Int. Cl.
*A61M 25/00*     (2006.01)
*A61B 17/00*     (2006.01)
(Continued)

(52) U.S. Cl.
CPC ......... *A61M 25/0009* (2013.01); *A61B 90/06* (2016.02); *A61B 2017/00526* (2013.01);
(Continued)

(58) Field of Classification Search
CPC ............... A61M 25/0009; A61B 90/06; A61B 18/1492; A61B 2017/00526;
(Continued)

(56) References Cited

U.S. PATENT DOCUMENTS 5,738,096 A     4/1998    Ben-Haim
5,827,273 A    10/1998    Edwards
(Continued)

FOREIGN PATENT DOCUMENTS

DE    10 2014 101348 A1    8/2015
EP         1201198 A1    5/2002
(Continued)

OTHER PUBLICATIONS

U.S. Appl. No. 62/934,077, filed Nov. 12, 2019, by Basu, et al., entitled: "Catheter With Vapor Deposited Features on Tip.".
(Continued)

*Primary Examiner* — Adam Z Minchella
*Assistant Examiner* — Abigail M Ziegler
(74) *Attorney, Agent, or Firm* — Lewis Roca Rothgerber Christie LLP

(57) ABSTRACT

A method is used to manufacture a surgical instrument. The surgical instrument includes a catheter and an end effector extending distally from the catheter. The method includes forming at least one electrode, sensor, or thermocouple onto the catheter or the end effector of the surgical instrument by etching or vapor depositing a three-dimensional structure onto a non-conductive material that is layered over a super elastic material.

19 Claims, 9 Drawing Sheets

(51) Int. Cl.
  *A61B 18/00* (2006.01)
  *A61B 18/14* (2006.01)
  *A61B 90/00* (2016.01)

(52) U.S. Cl.
  CPC ............ *A61B 2018/00083* (2013.01); *A61B 2018/00577* (2013.01); *A61B 2018/00619* (2013.01); *A61B 2018/00821* (2013.01); *A61B 18/1492* (2013.01); *A61B 2090/064* (2016.02); *A61B 2562/0261* (2013.01)

(58) Field of Classification Search
  CPC .......... A61B 2018/00083; A61B 2018/00577; A61B 2018/00619; A61B 2018/00821; A61B 2090/064; A61B 2562/0261; A61B 2034/2051; A61B 2218/002; A61B 2562/12; A61B 2562/125
  See application file for complete search history.

(56) References Cited

U.S. PATENT DOCUMENTS

| | | | |
|---|---|---|---|
| 5,843,019 A | 12/1998 | Eggers et al. | |
| 8,956,353 B2 | 2/2015 | Govari et al. | |
| 9,480,416 B2 | 11/2016 | Govari et al. | |
| 9,801,585 B2 | 10/2017 | Shah et al. | |
| 9,848,795 B2 | 12/2017 | Marecki et al. | |
| 9,907,480 B2 | 3/2018 | Basu et al. | |
| 10,130,422 B2 | 11/2018 | Ditter | |
| 10,602,983 B2 * | 3/2020 | Sterrett | A61B 5/6852 |
| 10,660,700 B2 | 5/2020 | Beeckler et al. | |
| 10,702,177 B2 | 7/2020 | Aujla | |
| 10,743,932 B2 | 8/2020 | Gallardo et al. | |
| 2002/0068934 A1 | 6/2002 | Edwards et al. | |
| 2011/0237935 A1 * | 9/2011 | Kalpin | A61B 34/20 600/424 |
| 2011/0288392 A1 * | 11/2011 | de la Rama | B23K 26/38 606/41 |
| 2014/0081111 A1 * | 3/2014 | Tun | A61B 5/287 600/374 |
| 2014/0350564 A1 | 11/2014 | Huszar et al. | |
| 2015/0351652 A1 * | 12/2015 | Marecki | A61B 18/1492 29/829 |
| 2016/0192982 A1 * | 7/2016 | Just | A61B 18/1492 606/46 |
| 2016/0354160 A1 * | 12/2016 | Crowley | A61B 10/04 |
| 2017/0112405 A1 * | 4/2017 | Sterrett | H05K 3/143 |
| 2017/0156784 A1 * | 6/2017 | Aujla | A61B 18/1492 |
| 2018/0000541 A1 * | 1/2018 | de la Rama | A61B 18/1492 |
| 2018/0071017 A1 | 3/2018 | Bar-Tal et al. | |
| 2018/0161577 A1 * | 6/2018 | Goedeke | A61M 25/10 |

FOREIGN PATENT DOCUMENTS

| | | | | |
|---|---|---|---|---|
| WO | WO-2016130713 A1 * | 8/2016 | ........ | A61B 18/1492 |
| WO | WO-2021078595 A1 * | 4/2021 | ........ | A46B 15/0012 |

OTHER PUBLICATIONS

PCT ISA Search Report dated Feb. 26, 2021, for International Application No. PCT/US2020/070769, 5 pages.
PCT ISA Written Opinion dated Feb. 26, 2021, for International Application No. PCT/US2020/070769, 8 pages.
PCT International Preliminary Report on Patentability dated May 17, 2022, for International Application No. PCT/US2020/070769, 7 pages.

* cited by examiner

CATHETER WITH VAPOR DEPOSITED FEATURES ON TIP

PRIORITY

This application claims priority to U.S. Provisional Patent Application Ser. No. 62/934,077, filed Nov. 12, 2019, entitled "Catheter With Vapor Deposited Features On Tip," the disclosure of which is incorporated by reference herein.

BACKGROUND

Cardiac arrhythmias, such as atrial fibrillation, occur when regions of cardiac tissue abnormally conduct electric signals. Procedures for treating arrhythmia include surgically disrupting the conducting pathway for such signals. By selectively ablating cardiac tissue by application of energy (e.g., radiofrequency (RF) energy), it may be possible to cease or modify the propagation of unwanted electrical signals from one portion of the heart to another. The ablation process may provide a barrier to unwanted electrical pathways by creating electrically insulative lesions or scar tissue that effectively block communication of aberrant electrical signals across the tissue.

In some procedures, a catheter with one or more RF electrodes may be used to provide ablation within the cardiovascular system. The catheter may be inserted into a major vein or artery (e.g., the femoral artery) and then advanced to position the electrodes within the heart or in a cardiovascular structure adjacent to the heart (e.g., the pulmonary vein). One or more electrodes may be placed in contact with cardiac tissue or other vascular tissue and then activated with RF energy to thereby ablate the contacted tissue. In some cases, the electrodes may be bipolar. In some other cases, a monopolar electrode may be used in conjunction with a ground pad or other reference electrode that is in contact with the patient that is in contact with the patient. Irrigation may be used to draw heat from ablating components of an ablation catheter; and to prevent the formation of blood clots near the ablation site.

Examples of ablation catheters are described in U.S. Pub. No. 2013/0030426, entitled "Integrated Ablation System using Catheter with Multiple Irrigation Lumens," published Jan. 31, 2013, the disclosure of which is incorporated by reference herein; U.S. Pub. No. 2017/0312022, entitled "Irrigated Balloon Catheter with Flexible Circuit Electrode Assembly," published Nov. 2, 2017, the disclosure of which is incorporated by reference herein; U.S. Pub. No. 2018/0071017, entitled "Ablation Catheter with a Flexible Printed Circuit Board," published Mar. 15, 2018, the disclosure of which is incorporated by reference herein; U.S. Pub. No. 2018/0056038, entitled "Catheter with Bipole Electrode Spacer and Related Methods," published Mar. 1, 2018, the disclosure of which is incorporated by reference herein; U.S. Pat. No. 10,130,422, entitled "Catheter with Soft Distal Tip for Mapping and Ablating Tubular Region," issued Nov. 20, 2018, the disclosure of which is incorporated by reference herein; U.S. Pat. No. 8,956,353, entitled "Electrode Irrigation Using Micro-Jets," issued Feb. 17, 2015, the disclosure of which is incorporated by reference herein; and U.S. Pat. No. 9,801,585, entitled "Electrocardiogram Noise Reduction," issued Oct. 31, 2017, the disclosure of which is incorporated by reference herein.

Some catheter ablation procedures may be performed after using electrophysiology (EP) mapping to identify tissue regions that should be targeted for ablation. Such EP mapping may include the use of sensing electrodes on a catheter (e.g., the same catheter that is used to perform the ablation or a dedicated mapping catheter). Such sensing electrodes may monitor electrical signals emanating from conductive endocardial tissues to pinpoint the location of aberrant conductive tissue sites that are responsible for the arrhythmia. Examples of an EP mapping system are described in U.S. Pat. No. 5,738,096, entitled "Cardiac Electromechanics," issued Apr. 14, 1998, the disclosure of which is incorporated by reference herein. Examples of EP mapping catheters are described in U.S. Pat. No. 9,907,480, entitled "Catheter Spine Assembly with Closely-Spaced Bipole Microelectrodes," issued Mar. 6, 2018, the disclosure of which is incorporated by reference herein; U.S. Pat. No. 10,130,422, entitled "Catheter with Soft Distal Tip for Mapping and Ablating Tubular Region," issued Nov. 20, 2018, the disclosure of which is incorporated by reference herein; and U.S. Pub. No. 2018/0056038, entitled "Catheter with Bipole Electrode Spacer and Related Methods," published Mar. 1, 2018, the disclosure of which is incorporated by reference herein.

When using an ablation catheter, it may be desirable to ensure that one or more electrodes of the ablation catheter are sufficiently contacting target tissue. For instance, it may be desirable to ensure that one or more electrodes are contacting target tissue with enough force to effectively apply RF ablation energy to the tissue; while not applying a degree of force that might tend to undesirably damage the tissue. To that end, it may be desirable to include one or more force sensors or pressure sensors to detect sufficient contact between one or more electrodes of an ablation catheter and target tissue.

In addition to using force sensing or EP mapping, some catheter ablation procedures may be performed using an image guided surgery (IGS) system. The IGS system may enable the physician to visually track the location of the catheter within the patient, in relation to images of anatomical structures within the patient, in real time. Some systems may provide a combination of EP mapping and IGS functionalities, including the CARTO 3® system by Biosense Webster, Inc. of Irvine, California Examples of catheters that are configured for use with an IGS system are disclosed in U.S. Pat. No. 9,480,416, entitled "Signal Transmission Using Catheter Braid Wires," issued Nov. 1, 2016, the disclosure of which is incorporated by reference herein; and various other references that are cited herein.

While several catheter systems and methods have been made and used, it is believed that no one prior to the inventors has made or used the invention described, illustrated and claimed herein.

BRIEF DESCRIPTION OF THE DRAWINGS

The drawings and detailed description that follow are intended to be merely illustrative and are not intended to limit the scope of the invention as contemplated by the inventors.

DETAILED DESCRIPTION FOR MODES OF CARRYING OUT THE INVENTION

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

I. Overview of Exemplary Ablation Catheter System

Figure 1:
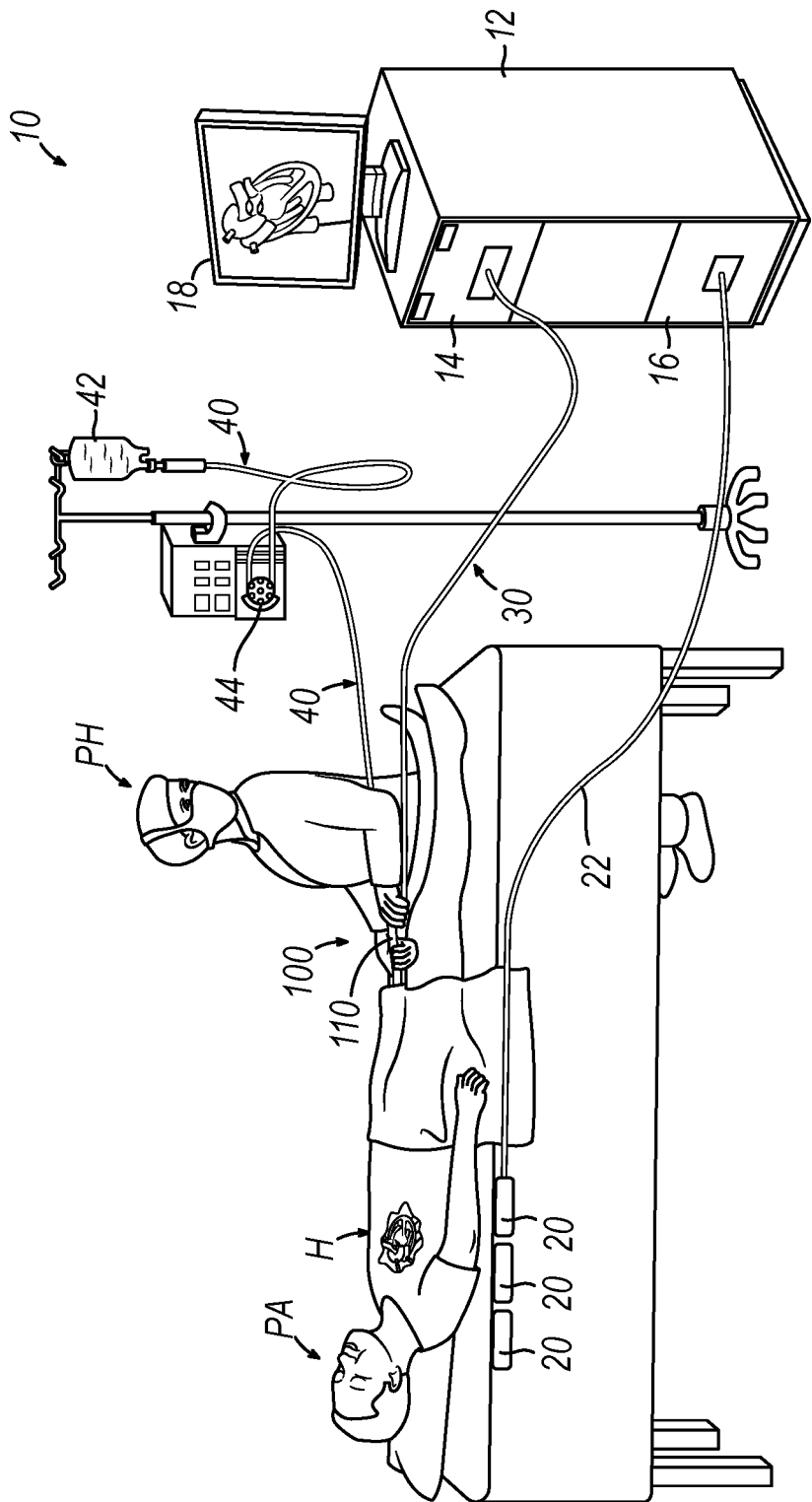
FIG. 1 depicts a schematic view of a medical procedure in which a catheter of a catheter assembly is inserted in a patient.
Figure 2:
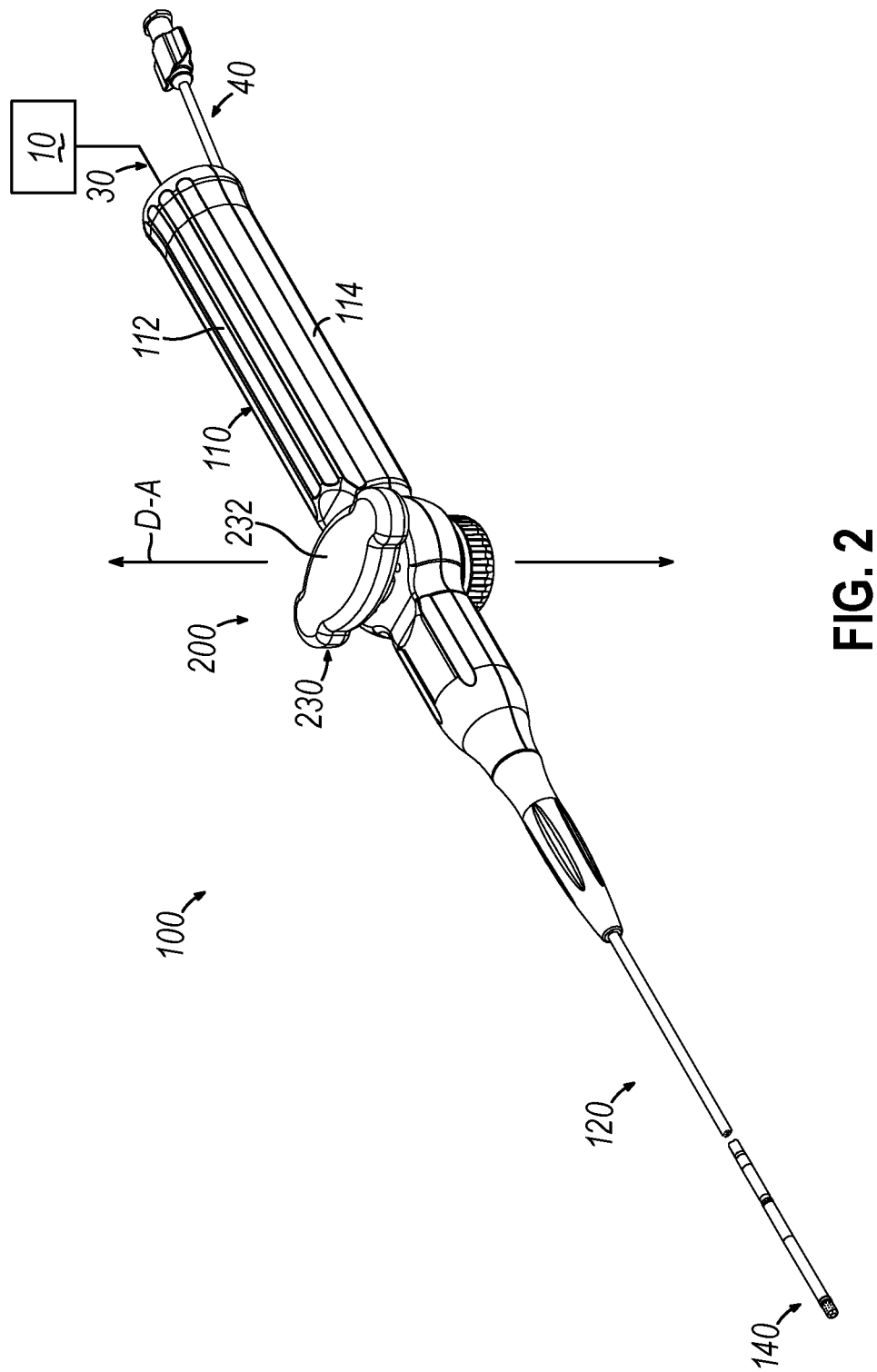
FIG. 2 depicts a perspective view of the catheter assembly of FIG. 1, with additional components shown in schematic form.

FIG. 1 shows an exemplary medical procedure and associated components of a cardiac ablation catheter system that may be used to provide cardiac ablation as referred to above. In particular, FIG. 1 shows a physician (PH) grasping a handle (110) of a catheter assembly (100), with an end effector (140) of a catheter (120) (shown in FIGS. 2-3 but not shown in FIG. 1) of catheter assembly (100) disposed in a patient (PA) to ablate tissue in or near the heart (H) of the patient (PA). As shown in FIG. 2, catheter assembly (100) includes handle (110), catheter (120) extending distally from handle (110), end effector (140) located at a distal end of catheter (120), and a deflection drive assembly (200) associated with handle (110).

As will be described in greater detail below, end effector (140) includes various components configured to deliver RF energy to targeted tissue sites, provide EP mapping functionality, track external forces imparted on end effector (140), track the location of end effector (140), and disperse irrigation fluid. As will also be described in greater detail below, deflection drive assembly (200) is configured to deflect end effector (140) and a distal portion of catheter (120) away from a central longitudinal axis (L-L) (FIGS. 3-5) defined by a proximal portion of catheter (120).

Figure 3:
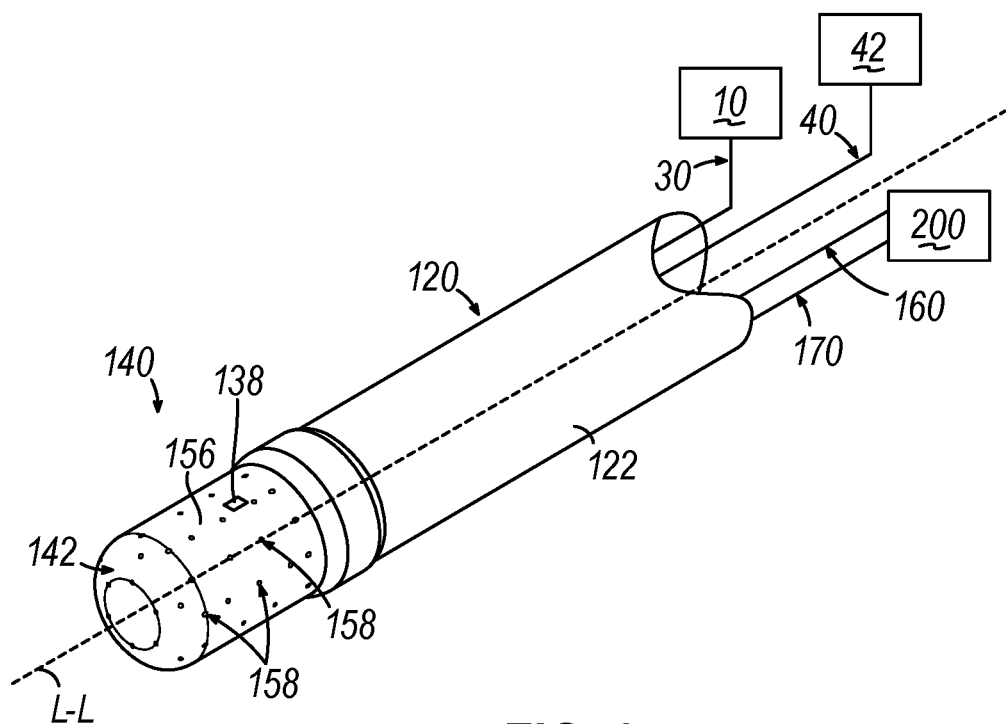
FIG. 3 depicts a perspective view of a distal portion of the catheter of FIG. 1, with additional components shown in schematic form.

As shown in FIG. 3, catheter (120) includes an elongate flexible sheath (122), with end effector (140) being disposed at a distal end of elongate flexible sheath (122). End effector (140) and various components that are contained in elongate flexible sheath (122) will be described in greater detail below. Catheter assembly (100) is coupled with a guidance and drive system (10) via a cable (30). Catheter assembly (100) is also coupled with a fluid source (42) via a fluid conduit (40). A set of field generators (20) are positioned underneath the patient (PA) and are coupled with guidance and drive system (10) via another cable (22). Field generators (20) are merely optional.

Guidance and drive system (10) of the present example include a console (12) and a display (18). Console (12) includes a first driver module (14) and a second driver module (16). First driver module (14) is coupled with catheter assembly (100) via cable (30). In some variations, first driver module (14) is operable to receive EP mapping signals obtained via microelectrodes (138) of end effector (140) as described in greater detail below. Console (12) includes a processor (not shown) that processes such EP mapping signals and thereby provides EP mapping as is known in the art.

First driver module (14) of the present example is further operable to provide RF power to a distal tip member (142) of end effector (140), as will be described in greater detail below, to thereby ablate tissue. Second driver module (16) is coupled with field generators (20) via cable (22). Second driver module (16) is operable to activate field generators (20) to generate an alternating magnetic field around the heart (H) of the patient (PA). For instance, field generators

(20) may include coils that generate alternating magnetic fields in a predetermined working volume that contains the heart (H).

First driver module (14) is also operable to receive position indicative signals from a position sensor assembly (150) in end effector (140). In such versions, the processor of console (12) is also operable to process the position indicative signals from position sensor assembly (150) to thereby determine the position of end effector (140) within the patient (PA). As will be described in greater detail below, position sensor assembly (150) includes a pair of coils on respective panels (151) that are operable to generate signals that are indicative of the position and orientation of end effector (140) within the patient (PA). The coils are configured to generate electrical signals in response to the presence of an alternating electromagnetic field generated by field generators (20). Other components and techniques that may be used to generate real-time position data associated with end effector (140) may include wireless triangulation, acoustic tracking, optical tracking, inertial tracking, and the like. Alternatively, end effector (140) may lack a position sensor assembly (150).

Display (18) is coupled with the processor of console (12) and is operable to render images of patient anatomy. Such images may be based on a set of preoperatively or intraoperatively obtained images (e.g., a CT or MM scan, 3-D map, etc.). The views of patient anatomy provided through display (18) may also change dynamically based on signals from position sensor assembly (150) of end effector (140). For instance, as end effector (140) of catheter (120) moves within the patient (PA), the corresponding position data from position sensor assembly (150) may cause the processor of console (12) to update the patient anatomy views in display (18) in real time to depict the regions of patient anatomy around end effector (140) as end effector (140) moves within the patient (PA). Moreover, the processor of console (12) may drive display (18) to show locations of aberrant conductive tissue sites, as detected via electrophysiological (EP) mapping with end effector (140) or as otherwise detected (e.g., using a dedicated EP mapping catheter, etc.). By way of example only, the processor of console (12) may drive display (18) to superimpose the locations of aberrant conductive tissue sites on the images of the patient's anatomy, such as by superimposing an illuminated dot, a crosshair, or some other form of visual indication of aberrant conductive tissue sites.

The processor of console (12) may also drive display (18) to superimpose the current location of end effector (140) on the images of the patient's anatomy, such as by superimposing an illuminated dot, a crosshair, a graphical representation of end effector (140), or some other form of visual indication. Such a superimposed visual indication may also move within the images of the patient anatomy on display (18) in real time as the physician moves end effector (140) within the patient (PA), thereby providing real-time visual feedback to the operator about the position of end effector (140) within the patient (PA) as end effector (140) moves within the patient (PA). The images provided through display (18) may thus effectively provide a video tracking the position of end effector (140) within a patient (PA), without necessarily having any optical instrumentation (i.e., cameras) viewing end effector (140). In the same view, display (18) may simultaneously visually indicate the locations of aberrant conductive tissue sites detected through EP mapping. The physician (PH) may thus view display (18) to observe the real time positioning of end effector (140) in relation to the mapped aberrant conductive tissue sites and in relation to images of the adjacent anatomical structures in the patient (PA).

Fluid source (42) of the present example includes a bag containing saline or some other suitable irrigation fluid. Conduit (40) includes a flexible tube that is further coupled with a pump (44), which is operable to selectively drive fluid from fluid source (42) to catheter assembly (100). As described in greater detail below, such irrigation fluid may be expelled through openings (158) of distal tip member (142) of end effector (140). Such irrigation may be provided in any suitable fashion as will be apparent to those skilled in the art in view of the teachings herein.

II. Exemplary End Effector of Catheter Assembly

Figure 4:
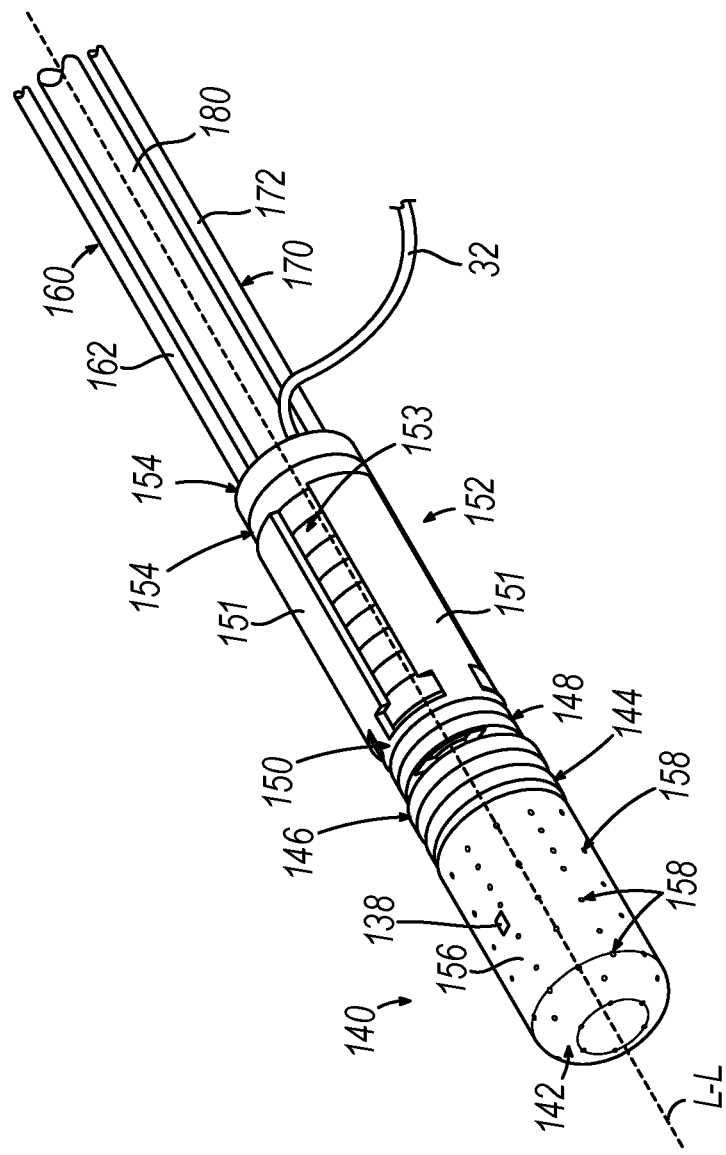
FIG. 4 depicts a perspective view of the distal portion of the catheter of FIG. 1, with an outer sheath omitted to reveal internal components.
Figure 5:
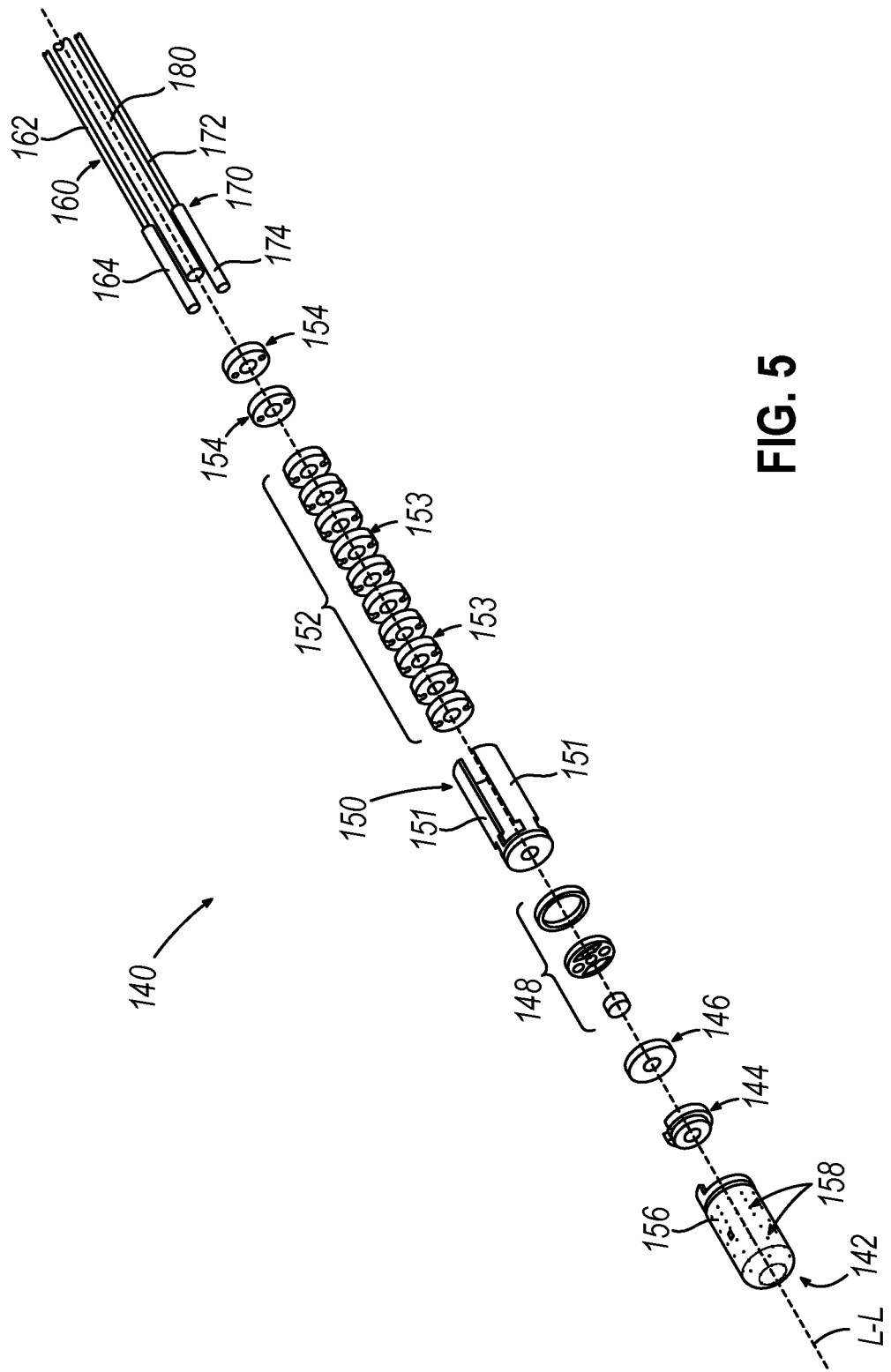
FIG. 5 depicts an exploded perspective view of the distal portion of the catheter of FIG. 1.

As mentioned above, end effector (140) includes various components configured to deliver RF energy to targeted tissue sites, provide EP mapping functionality, track external forces imparted on end effector (140), track the location of end effector (140) within the patient (PA), and disperse irrigation fluid. FIGS. 3-5 show exemplary components of end effector (140), and other components of the distal portion of catheter (120), in greater detail. End effector (140) includes a distal tip member (142), a distal tip base (144), a distal circuit disk (146), a force sensor assembly (148), a position sensor assembly (150), a distal spacer stack (152), and a pair of proximal spacers (154). Distal tip member (142), distal tip base (144), distal circuit disk (146), force sensor assembly (148), position sensor assembly (150), distal spacer stack (152), and proximal spacers (154) are coaxially aligned with each other and are stacked longitudinally so that these components (144-154) define a stacked circuit. A pair of push-pull cables (160, 170) and an irrigation tube (180) extend along the length of catheter (120) to reach end effector (140). Each of the foregoing components will be described in greater detail below. Flexible sheath (122) surrounds all of the foregoing components except for distal tip member (142).

As shown in FIGS. 4-5, distal tip member (142) of the present example includes a cylindraceous body (156) with a dome tip. Cylindraceous body (156) and the dome tip may be formed of an electrically conductive material, such as metal. A plurality of openings (158) are formed through cylindraceous body (156) and are in communication with the hollow interior of distal tip member (142). Openings (158) thus allow irrigation fluid to be communicated from the interior of distal tip member (142) out through cylindraceous body (156). Cylindraceous body (156) and the dome tip are also operable to apply RF electrical energy to tissue to thereby ablate the tissue. Such RF electrical energy may be communicated from first driver module (14) to the proximalmost spacer (154) via cable (30). Distal tip member (142) may also include one or more thermocouples that are configured to provide temperature sensing capabilities.

As shown in FIGS. 3-4, distal tip member (142) of the present example also includes one or more EP mapping microelectrodes (138) mounted to cylindraceous body (156). EP mapping microelectrodes (138) are configured to pick up electrical potentials from tissue that comes into contact with EP mapping microelectrodes (138). EP mapping microelectrodes (138) may thus be used to determine locations of aberrant electrical activity in tissue within a cardiovascular anatomical structure (e.g., pulmonary vein, etc.). Signals picked up by EP mapping microelectrodes (138) may be communicated through vias or other structures in the layers that are proximal to force sensor assembly (148), eventually reaching first driver module (14) of console (12) via cable (30). First driver module (14) may process the EP mapping signals and provide the physician (PH) with corresponding feedback indicating the locations of aberrant electrical activity in accordance with the teachings of various references cited herein.

In versions where cylindraceous body (156) is formed of an electrically conductive material to provide RF electrical energy for tissue ablation, an electrically insulating material may be interposed between cylindraceous body (156) and EP mapping microelectrodes (138) to thereby electrically isolate EP mapping microelectrodes (138) from cylindraceous body (156). EP mapping microelectrodes (138) may be constructed and operable in accordance with the teachings of various patent references cited herein. While only one EP mapping microelectrode (138) is shown, distal tip member (142) may include two or more EP mapping microelectrodes (138). Alternatively, distal tip member (142) may lack EP mapping microelectrodes (138) altogether.

Distal tip base (144) defines a central aperture configured to provide a path for communication of irrigation fluid to the hollow interior of distal tip member (142). Distaltip base (144) forms an annular shoulder that the proximal edge of distal tip member (142) may abut. Distal tip base (144) also defines a lateral notch that is configured to receive a proximally extending tab of distal tip member (142). As shown in FIGS. 3-4, distal circuit disk (146) is positioned proximal to distal tip base (144). Distal circuit disk (146) includes circuitry that is operable to communicate RF electrical energy to distal tip member (142) via the proximally extending tab of distal tip member (142). In versions where one or more EP mapping electrodes (138) are included, distal circuit disk (146) may also include circuitry that is operable to communicate EP mapping signals from EP mapping electrodes (138).

In some versions, distal circuit disk (146) further includes one or more transmission coils. Such transmission coils may provide wireless communication of signals (e.g., EP mapping signals from microelectrodes (138)) to one or more complementary coils that are proximal to distal circuit disk (146). In addition, or in the alternative, such transmission coils may provide wireless communication of RF electrical energy from one or more complementary coils that are proximal to distal circuit disk (146) to distal tip member (142). In versions where coils are incorporated into distal circuit disk (146) and one or more other layers that are proximal to force sensor assembly (148), such coils may thus enable wireless communication of electrical signals across force sensor assembly (148) without requiring wires, vias, or other electrically conductive structures to pass longitudinally across force sensor assembly (148).

In some versions, distal circuit disk (146) includes at least one transmission coil (TX) that is paired with receiving coil (RX) of position sensor assembly (150) to detect strain being applied to force sensor assembly (148) so as to determine the contact force applied to distal tip (142). Some other versions of distal circuit disk (146) may simply omit a TX coil.

Force sensor assembly (148) is positioned proximal to distal circuit disk (146) and is configured to sense external forces that impinge against distal tip member (142). When distal tip (142) encounters external forces (e.g., when distal tip (142) is pressed against tissue), those external forces are communicated from distal tip (142) to distal tip base (144), to distal circuit disk (146), and to force sensor assembly (148) such that strain gauge may generate a suitable signal corresponding to the magnitude and direction of the external force. The signals from force sensor assembly (148) may be communicated through vias or other structures in the layers that are proximal to force sensor assembly (148), eventually reaching first driver module (14) of console (12) via cable (30). First driver module (14) may process the strain signals in accordance with any suitable fashion as would be apparent to one of ordinary skill in the art in view of the teachings herein. By way of example only, console (12) may provide audible feedback to alert the physician (PH) when force sensor assembly (148) indicates that distal tip member (142) is encountering forces over a predetermined threshold, to thereby prevent the physician (PH) from unwittingly damaging a cardiovascular anatomical structure with distal tip member (142).

Position sensor assembly (150) may generate signals indicating the position and orientation of end effector (140) in three-dimensional space with substantial precision. Position sensor assembly (150) includes a plurality of panels (151), each including an RX coil that is operable to generate position-indicative electrical signals in response to the alternating magnetic fields generated by field generators (20). Each RX coil may be formed by electrical traces to define an electrical coil or antenna to receive radiofrequency signals emitted by external transmitters TX coils (e.g., three TX coils provided by field generators (20) positioned external of the patient (PA) body and emitting discrete radiofrequencies) such that the location and orientation of each RX coil can be determined with respect to the TX coils provided by field generators (20). The signals from position sensor assembly (150) may be communicated through vias or other structures in the layers that are proximal to strain position sensor assembly (150), eventually reaching first driver module (14) of console (12) via cable (30).

A central annular body of position sensor assembly (150) defines a central aperture configured to provide a path for communication of irrigation fluid to the hollow interior of distal tip member (142). In versions where central annular body of position sensor assembly includes wireless communication coils, such wireless communication coils may be further coupled with vias or other structures in the layers that are proximal to strain position sensor assembly (150), thereby providing a path for electrical communication with first driver module (14) of console (12) via cable (30).

In the present example, each distal spacer (153) is generally shaped like a disk, with a pair of chordal cutouts angularly offset from each other by 90 degrees. These cutouts are sized and configured to accommodate a respective panel (151) of position sensor assembly (150), thereby allowing panels (151) to be radially interposed between distal spacer stack (152) and sheath (122). Each distal spacer (153) also includes a pair of cable notches that are angularly offset from each other by 180 degrees. These cable notches are configured to receive a respective distal end portion (174, 164) of push-pull cables (160, 170). Each distal spacer (153) further includes a central aperture configured to provide a path for communication of irrigation fluid to the hollow interior of distal tip member (142).

Each proximal spacer (154) is shaped like a disk, with three apertures formed therethrough. A central aperture is configured to provide a path for communication of irrigation fluid to the hollow interior of distal tip member (142). The side apertures are sized and configured to receive proximal portions (162, 172) of a respective push-pull cable (160, 170).

As noted above and as shown in FIGS. 1 and 3, cable (30) couples catheter assembly (100) with drive system (10). As shown in FIG. 4, wires (32) of cable (30) extend along the length of catheter (120) to reach the proximal-most proximal spacer (154). Wires (32) may thus be contained within sheath (122). Wires (32) may be physically and electrically coupled with the proximal-most proximal spacer (154) in any suitable fashion.

As also noted above, catheter assembly (100) is configured to enable irrigation fluid to be communicated from fluid source (42) to catheter (120) via fluid conduit (40), thereby providing expulsion of the irrigation fluid via openings (158) of distal tip member (142). In the present example, the fluid path for the irrigation fluid includes an irrigation tube (180), which is shown in FIGS. 4-5. The proximal end of irrigation tube (180) is coupled with fluid conduit (40) (e.g., at handle (110) of catheter assembly (100)). Irrigation tube (180) extends along the length of catheter (120) to reach end effector (140). In some versions, irrigation fluid may be communicated from the distal end of irrigation tube (180) through the central passageway formed by the aligned by the above-mentioned central apertures, ultimately reaching the interior of distal tip member (142) via aperture (218) of distal tip base (144).

III. Exemplary Alternative Catheter and End Effector of Catheter Assembly

Flex circuit technology may include intricate manufacturing methods to transform a two-dimensional structure into a three-dimensional structure, precise adhesive applications, complex tooling, or one or more curing processes, etc. For structures such as openings (158) or to effectuate seamless transitions at assembly, conventional flex circuit technology may be difficult and sporadic especially when using scales below about 0.010 inches. Integrating sensing and therapeutic technologies in a single manufacturing process, overlaid onto a substrate with shape setting capabilities, may considerably simplify the manufacturability of the complex structures pertaining to the sensing and therapeutic technologies. Such a single manufacturing process may be desirable and may surpass conventional flex circuit technology.

An exemplary alternative catheter (310) and exemplary alternative end effector (312) are described in greater detail below. Catheter (310) and end effector (312) may be provided as an alternative to catheter (120) and end effector (140) described above. Catheter (310) and end effector (312) may provide benefits over a conventional two-dimensional flex circuit that is generally assembled in separate stages to arrive at a three-dimensional configuration. For example, assembly of a conventional two-dimensional flex circuit may generally utilize many components to be formed prior to elongate flexible sheath (122) being be slid over the components to form catheter (120).

A. Exemplary Alternative Catheter and End Effector

Figure 6:
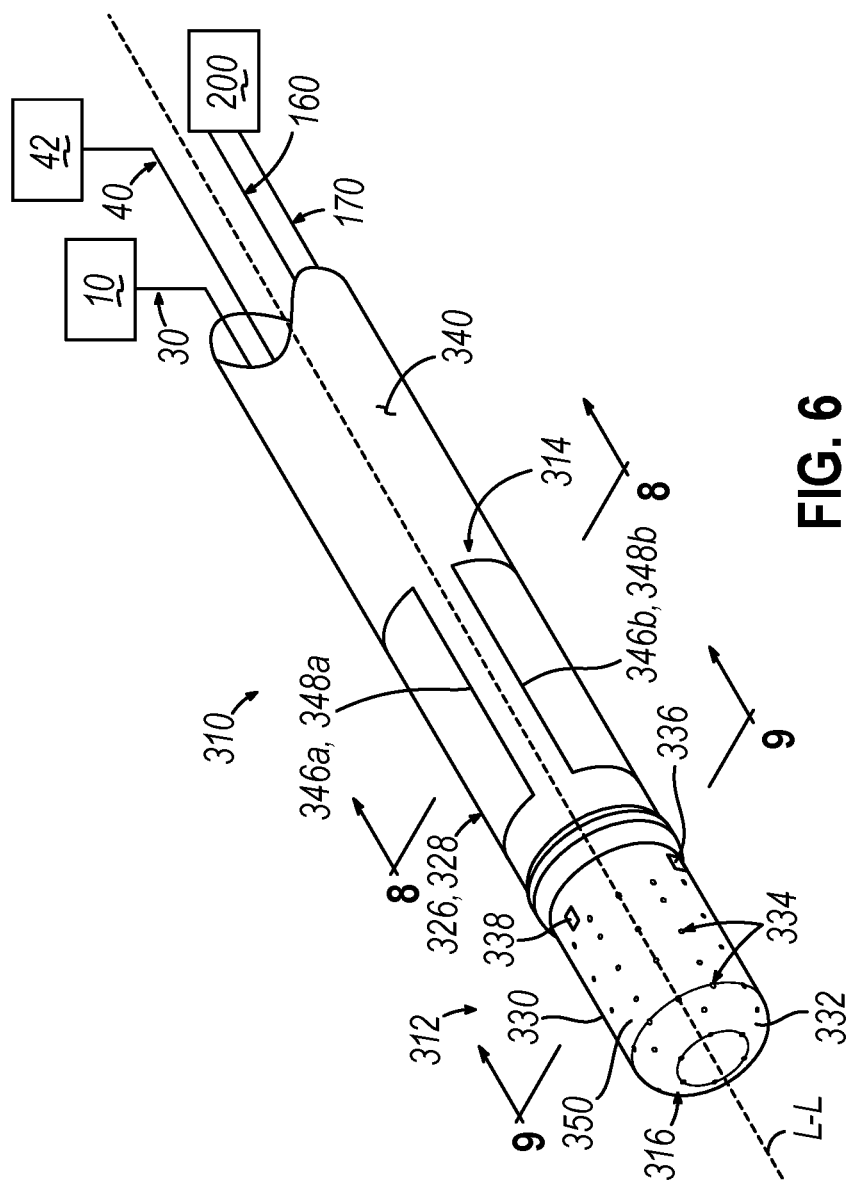
FIG. 6 depicts a schematic perspective view of a distal portion of an alternative catheter to the catheter of FIG. 1, where the catheter includes an elongate flexible sheath and the end effector includes a distal tip member with additional components shown in schematic form.
Figure 7:
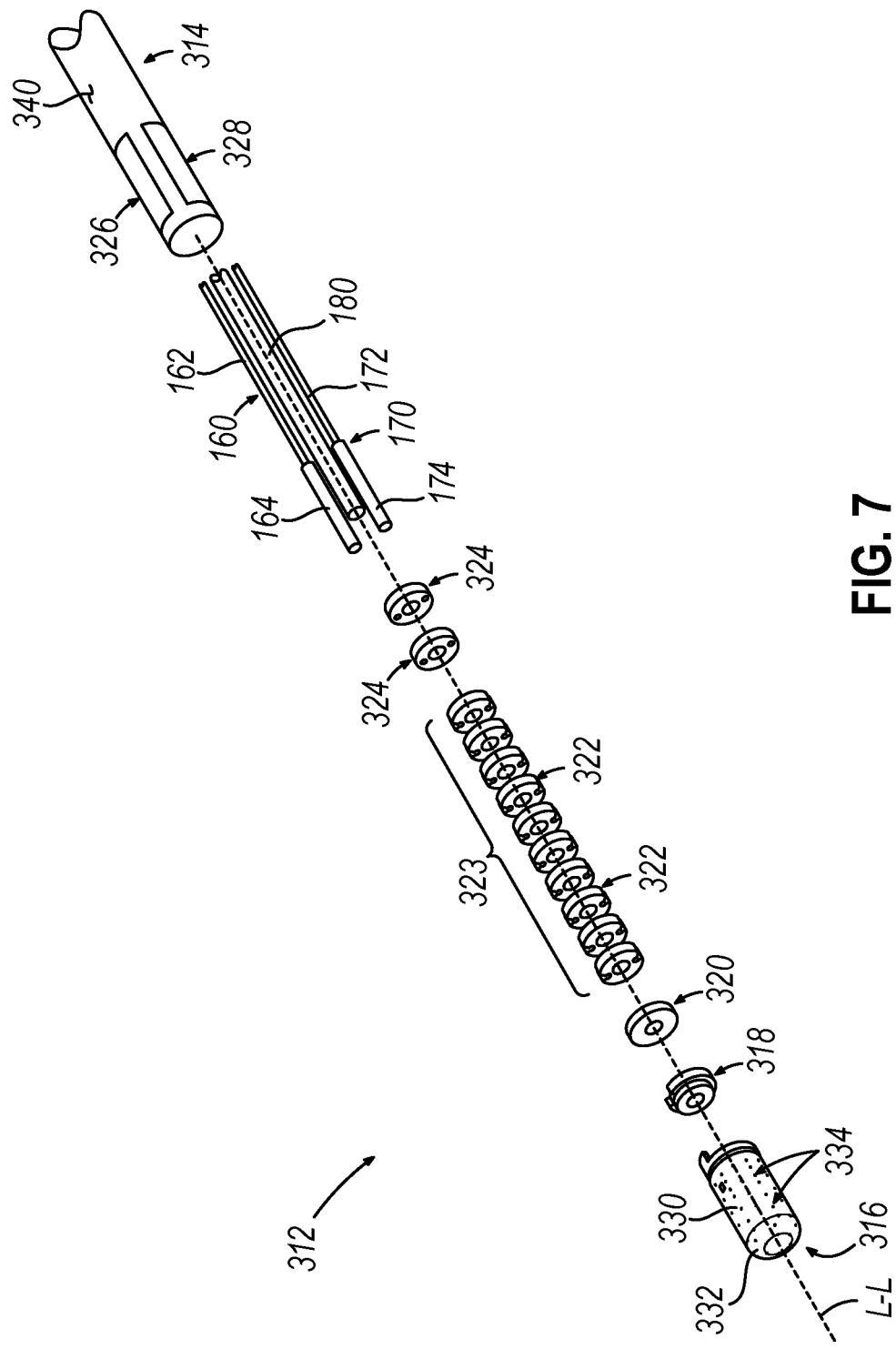
FIG. 7 depicts a schematic exploded perspective view of the distal portion of the catheter of FIG. 6.

FIG. 6 shows a perspective view of a distal portion of catheter (310) and end effector (312) for a surgical instrument (e.g., catheter assembly (100) as shown in FIGS. 1-2). As previously described with reference to FIGS. 1-3, catheter assembly (100) may include handle (110) and deflection drive assembly (200) associated with handle (110). In the present example, catheter assembly (100) includes catheter (310) and end effector (312), where catheter (310) extends distally from handle (110). As shown in FIG. 6, catheter (310) includes an elongate flexible sheath (314). End effector (312) is disposed at a distal end of elongate flexible sheath (314) of catheter (310). As will be described in greater detail with reference to FIGS. 6-11, catheter (310) is generally similar to catheter (120) and end effector (312) is generally similar to end effector (140) shown and described with reference to FIGS. 1-2, with differences described below. FIG. 7 shows an exploded perspective view of a distal portion of catheter (310) of FIG. 6, where catheter (310) defines a longitudinal axis (L-L).

FIGS. 6-7 show exemplary components of end effector (312), and other components of the distal portion of catheter (310), in greater detail. End effector (312) includes a distal tip member (316) similar to distal tip member (142), a distal tip base (318) similar to distal tip base (144), a distal circuit disk (320) similar to distal circuit disk (146), a distal spacer stack (322) similar to distal spacer stack (152) that includes distal spacers (323), and a pair of proximal spacers (324) similar to pair of proximal spacers (154). As shown, distal tip member (316), distal tip base (318), distal circuit disk (320), distal spacer stack (322), and proximal spacers (324) are coaxially aligned with each other and are stacked longitudinally so that these components (316-324) define a stacked circuit. Push-pull cables (160, 170) and irrigation tube (180) extend along the length of catheter (310) to reach end effector (312).

Distal tip member (316) includes a cylindraceous body (330) that includes a dome tip (332). Dome tip (332) of cylindraceous body (330) or entire cylindraceous body (330) may be formed of an electrically conductive material, such as metal. Cylindraceous body (330) with dome tip (332) is operable to apply RF electrical energy to tissue to thereby ablate the tissue. Such RF electrical energy may be communicated from first driver module (14) to the proximal-most spacer (324) via cable (30). A plurality of openings (334) are formed through cylindraceous body (330) and are in communication with the hollow interior of distal tip member (316). Openings (334) allow irrigation fluid to be communicated from the interior of distal tip member (316) out through cylindraceous body (330) of distal tip member (316).

Deflection drive assembly (200) is configured to deflect end effector (312) and a distal portion of catheter (310) away from a central longitudinal axis (L-L) (see FIGS. 6-7) defined by a proximal portion of catheter (310). As shown in FIG. 6, catheter (310) includes an elongate flexible sheath (314), with end effector (312) being disposed at a distal end of elongate flexible sheath (314). End effector (312) and various components that are contained in elongate flexible sheath (314) will be described in greater detail below. Catheter assembly (100) is coupled with guidance and drive system (10) via cable (30). Catheter assembly (100) is also coupled with fluid source (42) via fluid conduit (40).

As mentioned above and described below in greater detail with reference to FIGS. 8-9A, end effector (312) includes various components configured to perform one or more of delivering RF energy to targeted tissue sites, providing EP mapping functionality, tracking external forces imparted on end effector (312), tracking the position of end effector (312) within the patient (PA), or dispersing irrigation fluid. For this reason, end effector (312) may include one or more electrode(s), sensor(s), or thermocouple(s) (336). The electrode(s) may include at least one sensing electrode (e.g., an EP mapping electrode (338)), at least one ablation electrode (339), or at least one reference electrode (not shown). Separately, the sensor(s) may include at least one force sensor assembly (326) or at least one position sensor assembly (328). For example, unlike end effector (140), end effector (312) may include at least one etched or vapor deposited force sensor assembly (326) that may be used instead of or in addition to force sensor assembly (148); or at least one etched or vapor deposited position sensor assembly (328) that may be used instead of or in addition to position sensor assembly (150).

Figure 8A:
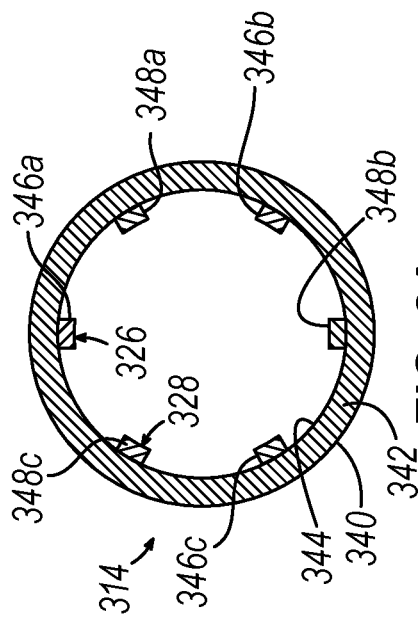
FIG. 8A depicts a schematic cross-sectional view of an exemplary alternative elongate flexible sheath similar to the elongate flexible sheath of FIG. 8, but where the force sensor is disposed on an inner surface of the elongate flexible sheath.
Figure 9A:
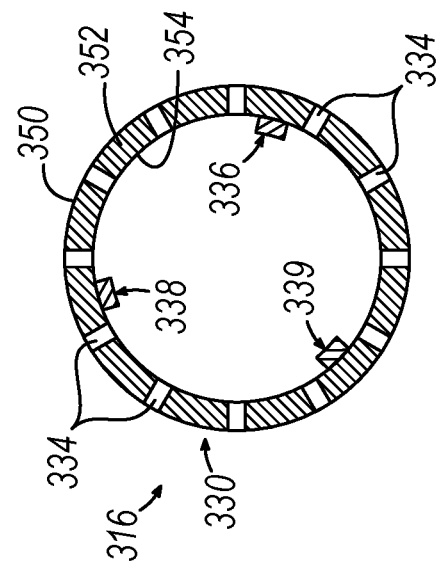
FIG. 9A depicts a schematic cross-sectional view of an exemplary alternative cylindraceous body similar to the cylindraceous body of FIG. 6 taken across line 9-9 of FIG. 6, but where the microelectrode and the thermocouple are disposed on an inner surface of the distal tip member.
Figure 8:
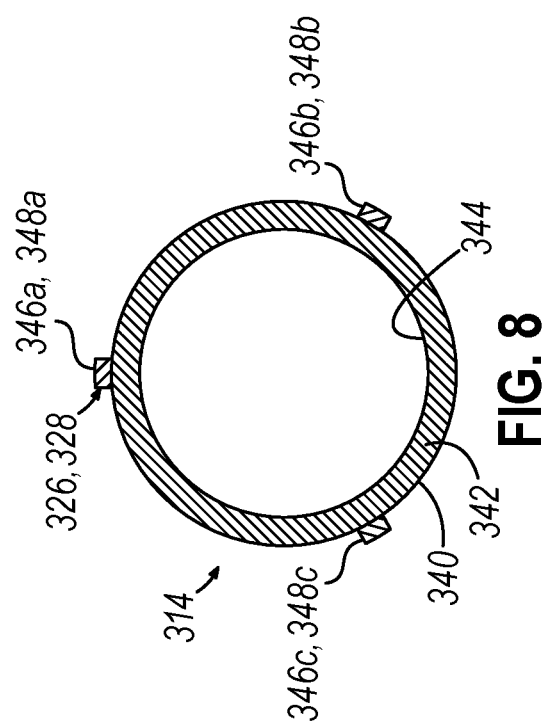
FIG. 8 depicts a schematic cross-sectional view of the elongate flexible sheath of the catheter of FIG. 6 taken across line 8-8 of FIG. 6, where the force sensor is disposed on an outer surface of the flexible elongate sheath.
Figure 9:
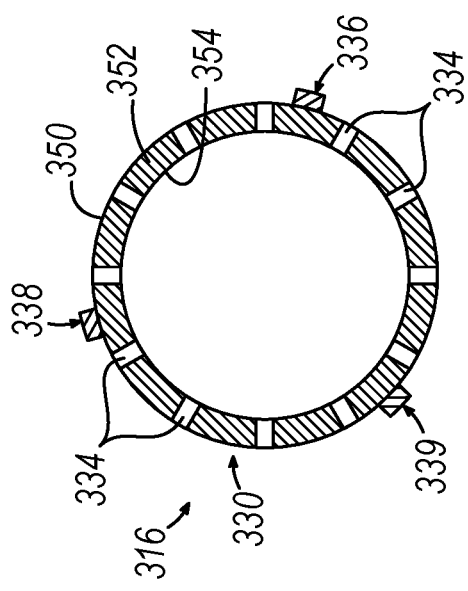
FIG. 9 depicts a schematic cross-sectional view of the cylindraceous body of FIG. 6 taken across line 9-9 of FIG. 6, where a microelectrode and a thermocouple are disposed on an outer surface of the distal tip member.

FIGS. 8 and 9 show two cross-sectional schematic views of FIG. 6. More specifically, FIG. 8 shows a cross-sectional view of elongate flexible sheath (314) of catheter (310) of FIG. 6 taken across line 8-8 of FIG. 6, where force sensor assembly (326) and position sensor assembly (328) are disposed on an outer surface (340) of a wall (342) of elongate flexible sheath (314) of catheter (310). FIG. 8A shows a cross-sectional view of an exemplary alternative elongate flexible sheath (314) similar to elongate flexible sheath (314) of FIG. 8, but where force sensor assembly (326) is disposed on an inner surface (344) of wall (342) of elongate flexible sheath (314) of catheter (310).

Force sensor assembly (326) is configured to sense external forces that impinge against distal tip member (316). When distal tip member (316) encounters external forces (e.g., when distal tip member (316) is pressed against tissue), those external forces are communicated from distal tip member (316) to distal tip base (318), to distal circuit disk (320), and to force sensor assembly (326), such that force sensor assembly (326) may generate a suitable signal corresponding to the magnitude and direction of the external force. The signals from force sensor assembly (148) may be communicated through vias or other structures in the layers that are proximal to force sensor assembly (326), eventually reaching first driver module (14) of console (12) via cable (30).

Force sensor assembly (326) may include multiple force sensors. For example, force sensor assembly (326) may include first, second, and third force sensors (346*a-c*). As shown in FIG. 8, first, second, and third force sensors (346*a-c*) may be etched or vapor deposited onto outer surface (340) of elongate flexible sheath (314) of catheter (310). Alternatively, as shown in FIG. 8A, first, second, and third force sensors (346*a-c*) may be etched or vapor deposited onto inner surface (344) of elongate flexible sheath (314) of catheter (310). It is also envisioned that force sensor assembly (326) (e.g. first, second, and third force sensors (346*a-c*)) may be etched or vapor deposited directly onto outer surface (340) or directly onto inner surface (344) of elongate flexible sheath (314). First, second, and third force sensors (346*a-c*) of force sensor assembly (326) may form a Rosette strain gauge (e.g. a three-direction Rosette strain gauge) vapor deposited onto outer surface (340) or inner surface (344) of elongate flexible sheath (314). Alternatively, force sensors (346*a-c*) may take any other suitable form as will be apparent to those skilled in the art in view of the teachings herein.

Position sensor assembly (328) is operable to generate signals that are indicative of the position and orientation of end effector (312) within the patient (PA) in a three-dimensional space. Position sensor assembly (328) may include one or more position sensors (e.g. position coils). For example, position sensor assembly (328) may include first, second, and third position coils (348*a-c*). As shown in FIG. 8, first, second, and third position coils (348*a-c*) may be etched or vapor deposited onto outer surface (340) of elongate flexible sheath (314). Alternatively, as shown in FIG. 8A, first, second, and third position coils (348*a-c*) may be etched or vapor deposited onto inner surface (344) of elongate flexible sheath (314). Each position coil (348*a-c*) may be oriented about an axis that is orthogonal to the axes of the other position coils (348*a-c*). Position sensor assembly (328) (e.g. first, second, and third position coils (348*a-c*)) may be etched or vapor deposited directly onto outer surface (340) or directly onto inner surface (344) of elongate flexible sheath (314). First, second, and third position coils (348*a-c*) of position sensor assembly (328) may be used instead of or in addition to plurality of panels (151) of position sensor assembly (150) shown and described with reference to FIGS. 4-5.

Force sensor assembly (326) may be formed together with, or formed separate from, position sensor assembly (328). FIG. 8 shows first force sensor (346*a*) combined with first position coil (348*a*), second force sensor (346*b*) combined with second position coil (348*b*), and third force sensor (346*c*) combined with third position coil (348*c*). For example, force sensor assembly (326) may be formed together as a single unitary structure together with position sensor assembly (328), such that first, second, and third force sensors (346*a-c*) are formed together as a unitary piece with first, second, and third position coils (348*a-c*) respectively. Alternatively, FIG. 8A shows first force sensor (346*a*) formed separate from first position coil (348*a*), second force sensor (346*b*) formed separate from second position coil (348*b*), and third force sensor (346*c*) formed separate from third position coil (348*c*). While not shown, it is envisioned that first, second, and third force sensors (346*a-c*) may be separate from first, second, and third position coils (348*a-c*) on outer surface (340) of elongate flexible sheath (314); or that first, second, and third force sensors (346*a-c*) may be combined with first, second, and third position coils (348*a-c*) on inner surface (344) of elongate flexible sheath (314).

Each position coil (348*a-c*) may be configured to generate electrical signals in response to the presence of an alternating electromagnetic field generated by field generators (20). Each position coil (348*a-c*) may be coupled with a corresponding trace (not shown) or other electrical conduit on elongate flexible sheath (314) of catheter (310), thereby enabling signals generated by position coils (348*a-c*) to be communicated back through electrical conduits (not shown) in catheter (310) to console (12), which may process the signals to identify the position end effector (312) within the patient (PA). For example, each position coil (348*a-c*) may be formed by electrical traces to define an electrical coil or antenna to receive radiofrequency signals emitted by external transmitters TX coils (e.g., three TX coils provided by field generators (20) positioned external of the body of patient (PA) and emitting discrete radiofrequencies), such that the location and orientation of each RX coil may be determined with respect to the TX coils provided by field generators (20). The signals from position sensor assembly (328) may be communicated through vias or other suitable structures in the layers that are proximal to position sensor assembly (328), eventually reaching first driver module (14) of console (12) via cable (30). While not shown, other components and techniques that may be used to generate real-time position data associated with end effector (312) may include wireless triangulation, acoustic tracking, optical tracking, inertial tracking, and the like.

FIG. 9 shows a cross-sectional view of cylindraceous body (330) of distal tip member (316) of FIG. 6 taken across line 9-9 of FIG. 6, where mapping electrode (338) (e.g. which may be similar to EP mapping microelectrode (138)), ablating electrode (339), and thermocouple (336) are disposed on an outer surface (350) of a wall (352) of cylindraceous body (330) of distal tip member (316). FIG. 9A shows a cross-sectional view of an exemplary alternative cylindraceous body (330) similar to cylindraceous body of FIG. 6 taken across line 9-9 of FIG. 6, but where mapping electrode (338), ablating electrode (339), and thermocouple (336) are disposed on inner surface (354) of cylindraceous body (330) of distal tip member (316). Thermocouple (336) (shown schematically) is configured to provide temperature sensing capabilities.

While only one mapping electrode (338) is shown in FIGS. 9-9A, more than one mapping electrode (338) may be incorporated. For example, a pair of mapping electrodes (338) may be utilized, and collectively considered a single "sensor." Each mapping electrode (338) may be coupled with a corresponding trace or other electrical conduit on elongate flexible sheath (314) of catheter (310), thereby enabling signals picked up by mapping electrode (338) to be communicated back through electrical conduits (not shown) in catheter (310) to console (12), which may process the signals to provide EP mapping to thereby identify locations of aberrant electrical activity within the cardiac anatomy. This may, in turn, allow the physician (PH) to identify the most appropriate regions of cardiac tissue to ablate (e.g., with RF energy, cryoablation, etc.), to thereby prevent or at least reduce the communication of aberrant electrical activity across the cardiac tissue. Such contact may be further promoted by providing a substantial number of mapping electrodes (338) on cylindraceous body (330) of distal tip member (316), as shown in FIGS. 9-9A. Having a substantial number of mapping electrodes (338) may enable end effector (312) to provide high density EP mapping through all four chambers of the heart (H), as several pairs of mapping electrodes (338) can provide electrocardiogram signal sensing at multiple regions of cardiac tissue simultaneously.

At least one ablation electrode (339) may be used to apply RF energy to tissue that is in contact with ablation electrode (339), to thereby ablate the tissue. Each ablation electrode (339) may be coupled with a corresponding trace or other electrical conduit on cylindraceous body (330) of distal tip member (316), thereby enabling console (12) to communicate RF energy through electrical conduits (not shown) in catheter (120) to the traces or other conduits on cylindraceous body (330) of distal tip member (316) to reach ablation electrodes (339). As with mapping electrode (338), the number and positioning of ablation electrode (339) as shown in FIG. 9-9A is merely illustrative. Any other suitable number or positioning may be used for ablation electrode (339). As yet another merely illustrative variation, ablation electrode (339) may be omitted from end effector (312). In some such variations, mapping electrode (338) may still be included on end effector (312).

B. Exemplary Structure Formed by Etching or Vapor Deposition

Figure 10:
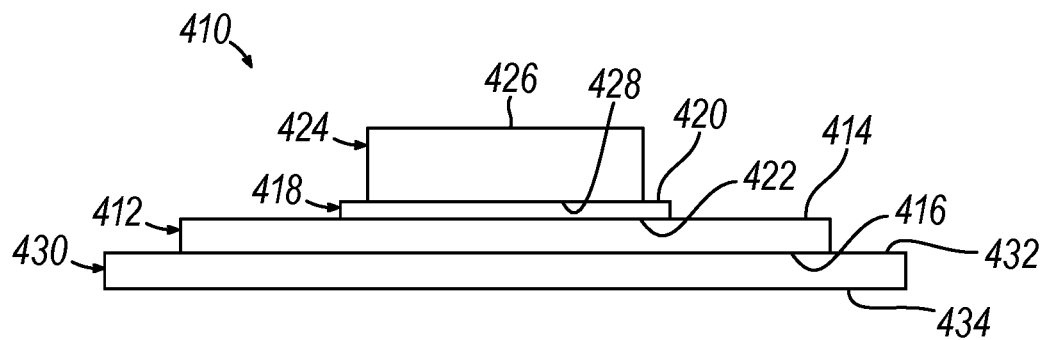
FIG. 10 depicts a schematic side elevational view of an exemplary structure utilizing etching or vapor deposition for the catheter or the end effector of FIG. 6.

FIG. 10 of an exemplary structure (410) formed by etching or vapor deposition that is suitable for at least one electrode, at least one sensor, or at least one thermocouple of FIG. 6. For example, force sensor assembly (326), position sensor assembly (328), thermocouple (336), mapping electrode (338), and ablation electrode (339), may be etched or vapor deposited on either elongate flexible sheath (314) of catheter (310) or cylindraceous body (330) of distal tip member (316) in the manner described below with reference to structure (410). For example, force sensors (346a-c) or position coils (348a-c) may be vapor deposited onto outer surface (340) or inner surface (344) of wall (342) of elongate flexible sheath (314) of catheter (310), thereby reducing or altogether eliminating, incorporating a separate force sensor or position coil. For example, thermocouple (336), mapping electrode (338), or ablation electrode (339) may be vapor deposited onto outer surface (350) or inner surface (354) of wall (352) of cylindraceous body (330) of distal tip member (316), thereby reducing or altogether eliminating additional structures.

As shown, structure (410) may include a first layer (412) having upper and lower surfaces (414, 416). First layer (412) is formed at least in part from a super elastic material, as described in greater detail below. The super elastic material may include a super elastic alloy. For example, the super elastic alloy may include nitinol. Nitinol may be provided as a thin film (e.g. one or more nitinol strips or other nitinol structures). In the present example, even to the extent that the material forming first layer (412) is electrically conductive, first layer (412) may primarily serve a structural purpose instead of serving an electrical or conductive purpose.

A second layer (418) having upper and lower surfaces (420, 422) is disposed over first layer (412). As shown, upper surface (414) of first layer (412) directly contacts a lower surface (422) of second layer (418). Second layer (418) is formed at least in part from an electrically non-conductive planar material. The non-conductive material offers electrically insulative properties between first layer (412) and a third layer (424). Third layer (424), having upper and lower surfaces (426, 428), is disposed over second layer (418). As shown, upper surface (420) of second layer (418) directly contacts a lower surface (428) of third layer (424). Third layer (424) includes an etched or vapor deposited material that is electrically conductive. In versions where third layer (424) is formed in several discrete zones that are separated from each other, second layer (418) may electrically isolate these separate zones of third layer (424) from each other (in addition to second layer (418) electrically isolating the zones of third layer (424) from first layer (412)). By way of example only, third layer (424) may include several discrete electrodes that are used for ablation or EP mapping, pressure sensors, or other suitable kinds of features. All layers (412, 418, 424) may also include other features such as fluid pathways, etc.

By way of example only, first layer (412) may include one or more nitinol strips or other nitinol structures. One or more nitinol strips may be applied to a substrate (430). A suitable substrate (430) includes, for example, elongate flexible sheath (314) of catheter (310) or cylindraceous body (330) of distal tip member (316). In other words, sheath (314) or cylindraceous body (330) may provide substrate (430) of FIG. 10. Substrate (430) includes upper and lower surfaces (432, 434). As shown, lower surface (416) of first layer (412) directly contacts upper surface (432) of substrate (430). The denotations of upper and lower surfaces are merely used for exemplary purposes, it is envisioned, that first layer (412) may directly contact and inner or outer surface of substrate (430). In versions where mapping and ablation electrodes (338, 339) are provided on outer surface (350) or inner surface (354) of cylindraceous body (330) of distal tip member (316), the nitinol strips or other resilient members may be interposed between layers of flexible material (e.g., polyimide, polyether ether ketone, etc.) forming elongate flexible sheath (314) or cylindraceous body (330). Alternatively, the nitinol strips or other resilient members may be positioned along regions of elongate flexible sheath (314) or cylindraceous body (330) where mapping and ablation electrodes (338, 339) are not present. While first layer (412) is applied to a substrate (430) layer in the foregoing example, other versions may omit substrate (430) altogether. In other words, first layer (412) may itself serve as a suitable substrate for the other layers (418, 424). In some such versions, first layer (412) may be formed in the shape of a cylinder, a cylinder with a flap that folds over to form a dome tip, or any other suitable shape.

As still another merely illustrative example, mapping and ablation electrodes (338, 339) and position coils (348a-c) may be applied directly onto an electrically insulative layer provided over the nitinol of cylindraceous body (330) of distal tip member (316). In such versions, end effector (312) may lack polyimide, polyether ether ketone, or other flexible materials that serve as conventional flex circuit substrates. Other methods may also be employed to provide mapping and ablation electrodes (338, 339), conductive traces, or other circuit components on outer and inner surfaces (340, 344) of elongate flexible sheath (314) of catheter (310) or on outer and inner surfaces (350, 354) of cylindraceous body (330) of distal tip member (316), including, but not limited to, sputter deposition, thermal deposition, etc.

End effector (312) may include any suitable number and arrangement of thermocouples like thermocouple (336). In addition, or in the alternative, end effector (312) may include any suitable number and arrangement of mapping electrodes (338). In addition, or in the alternative, end effector (312) may include any suitable number and arrangement of ablation electrodes like ablation electrode (339). In addition, or in the alternative, catheter (310) may include any suitable number and arrangement of force sensors like force sensors (346a-c). In addition, or in the alternative, catheter (310) may include any suitable number and arrangement of position sensors like position coils (348a-c). Other suitable ways in which catheter (310) and end effector (312) may be formed will be apparent to those skilled in the art in view of the teachings herein.

C. Exemplary Method of Manufacture

Figure 11:
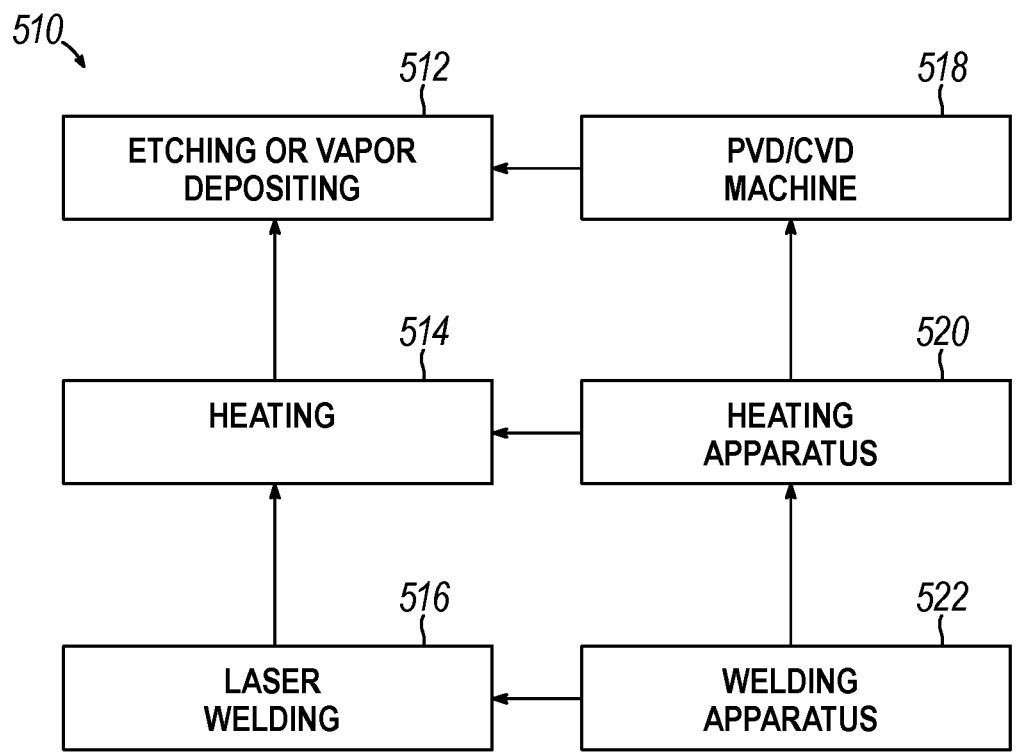
FIG. 11 depicts an exemplary method of forming the structure of FIG. 10.

FIG. 11 shows an exemplary method (510) of manufacturing a surgical instrument (e.g. catheter assembly (100) shown in FIGS. 1-2) that may include steps (512, 514, 516). As previously described, catheter assembly (100) includes catheter (310) and end effector (312) extending distally from catheter (310).

At step (512), method (510) may include forming at least one electrode, at least one sensor, or at least one thermocouple (336) by etching or vapor depositing a three-dimensional structure (e.g., third layer (424)) onto a non-conductive material (e.g., second layer (418)) that is layered over a super elastic material (e.g., first layer (412)). The at least one electrode may include at least one sensing electrode (e.g., EP mapping electrode (338)), or at least one ablation electrode (339), at least one reference electrode (not shown). Separately, the at least one sensor may include at least one force sensor assembly (326) or at least one position sensor assembly (328).

For example, the vapor depositing may be physical vapor depositing. Physical vapor deposition (PVD) (sometimes considered a thin film process) is an atomistic deposition process, where material is vaporized from a solid or liquid source into atoms or molecules and transported as a vapor through a vacuum or low pressure gaseous (or plasma) environment to a substrate, where the vapor condenses. The main categories of PVD processing are vacuum deposition (evaporation), sputter deposition, arc vapor deposition, and ion plating. Alternatively, the vapor depositing being chemical vapor depositing. Chemical vapor deposition (CVD) is a process in which film of materials are deposited from the vapor phase by the decomposition of chemicals on the surface of a substrate. The process is generally thermally driven, photo-assisted, or plasma-assisted. The deposition of the film is controlled by a chemical reaction. For example, a PVD or CVD machine (518) may be utilized.

First, second, and third layers (412, 418, 424) may create a single structure that is compatible with MM machines with both diagnostic and therapeutic capabilities. Step (512) may include etching or vapor depositing a dome, a barrel, a combination of a dome and a barrel, or a barrel with a dome tip. A magnetic material (e.g., third layer (424)) may be vapor deposited onto the non-conductive material (e.g., second layer (418)) to form structure (410).

At step (514), method (510) may include heat treating structure (410) to shape set structure (410) after the forming step. For example, a heating apparatus (520) may be utilized. This heat-treating step is merely optional. The super elastic material (for example, but not limited to, nitinol) allows for structure (410) to be shape set using one or more heat treatments to provide consistency in manufacturing.

At step (516), method (510) may include laser welding a seam or junction structure (410) to form a closed shape. For example, a welding apparatus (522) may be utilized. This laser welding step is merely optional. Existing microstructures (e.g., openings (334)) may be left untouched. As previously described, openings (334) allow irrigation fluid to be communicated from the interior of distal tip member (316) out through cylindraceous body (330) of distal tip member (316). Moreover, traces and bond pads may be deposited along appropriate layers, with wires being connected to the bond pads, to provide a path for electrical communication between end effector (312) and guidance and drive system (10).

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

EXAMPLE 1

A method of manufacturing a surgical instrument, the surgical instrument including a catheter and an end effector extending distally from the catheter, the method comprising: forming at least one electrode, sensor, or thermocouple onto the catheter or the end effector of the surgical instrument by etching or vapor depositing a three-dimensional structure onto a non-conductive material that is layered over a super elastic material.

EXAMPLE 2

The method of Example 1, the non-conductive material being planar.

EXAMPLE 3

The method of any one or more of Examples 1 through 2, the super elastic material comprising a super elastic alloy.

EXAMPLE 4

The method of Example 3, the super elastic alloy comprising nitinol.

EXAMPLE 5

The method of Example 4, the nitinol being in the form of a thin film.

EXAMPLE 6

The method of Example 1, the step of forming at least one electrode, sensor, or thermocouple onto the catheter or the end effector further comprising forming at least one electrode by etching or vapor depositing.

EXAMPLE 7

The method of Example 6, the at least one electrode being selected from the group consisting of a sensing electrode, an ablating electrode, and a reference electrode.

EXAMPLE 8

The method of any one or more of Examples 1 through 7, the step of forming at least one electrode, sensor, or thermocouple onto the catheter or the end effector further comprising forming at least one thermocouple by etching or vapor depositing.

EXAMPLE 9

The method of any one or more of Examples 1 through 8, the step of forming further comprising creating a single structure with both diagnostic and therapeutic capabilities.

EXAMPLE 10

The method of any one or more of Examples 1 through 9, the step of forming at least one electrode, sensor, or thermocouple onto the catheter or the end effector further comprising forming at least one sensor by etching or vapor depositing.

EXAMPLE 11

The method of any one or more of Examples 1 through 10, the sensor being at least one position sensor assembly or at least one force sensor assembly.

EXAMPLE 12

The method of Example 11, the catheter having inner and outer surfaces, the end effector having inner and outer surfaces, the position sensor assembly including at least one position coil, the step of forming further comprising etching or vapor depositing the at least one position coil onto at least one of the inner surface of the catheter, the inner surface of the end effector, the outer surface of the catheter, or the outer surface of the end effector

EXAMPLE 13

The method of Example 11, the position sensor assembly including at least one position coil, the step of forming further comprising etching or vapor depositing the at least one position coil onto an inner surface of the catheter or an inner surface of the end effector.

EXAMPLE 14

The method of Example 11, the position sensor assembly including at least one position coil, the step of forming further comprising etching or vapor depositing the at least one position coil onto an outer surface of the catheter or an outer surface of the end effector.

EXAMPLE 15

The method of Example 11, the at least one force sensor including a first force sensor, the step of forming further comprising etching or vapor depositing the first force sensor onto an inner surface of the catheter or an inner surface of the end effector.

EXAMPLE 16

The method of Example 15, the at least one force sensor further comprising a second force sensor, the step of forming further comprising etching or vapor depositing the second force sensor onto an inner surface of the catheter or an inner surface of the end effector.

EXAMPLE 17

The method of Example 16, the at least one force sensor further comprising a third force sensor, the step of forming further comprising etching or vapor depositing the second force sensor onto an inner surface of the catheter or an inner surface of the end effector.

EXAMPLE 18

The method of Example 11, the at least one force sensor including a first force sensor, the step of forming further comprising etching or vapor depositing the first force sensor onto an outer surface of the catheter or the end effector.

EXAMPLE 19

The method of Example 18, the at least one force sensor further comprising a second force sensor, the step of forming further comprising etching or vapor depositing the second force sensor onto an outer surface of the catheter or the end effector.

EXAMPLE 20

The method of Example 19, the at least one force sensor further comprising a third force sensor, the step of forming further comprising etching or vapor depositing the second force sensor onto an outer surface of the catheter or the end effector.

EXAMPLE 21

The method of any one or more of Examples 11 through 20, the at least one force sensor further comprising a Rosette strain gauge, vapor depositing the force sensor further comprising vapor depositing the Rosette strain gauge onto the catheter or the end effector.

EXAMPLE 22

The method of Example 21, the Rosette strain gauge being a three direction Rosette strain gauge, the vapor depositing the Rosette strain gauge further comprising vapor depositing the three direction Rosette strain gauge onto the catheter or the end effector.

EXAMPLE 23

The method of any one or more of Examples 1 through 22, the vapor depositing being physical vapor depositing.

EXAMPLE 24

The method of any one or more of Examples 1 through 22, the vapor depositing being chemical vapor depositing.

EXAMPLE 25

The method of any one or more of Examples 1 through 24, further comprising vapor depositing a magnetic material onto the non-conductive material to form the three-dimensional structure.

EXAMPLE 26

The method of any one or more of Examples 1 through 25, further comprising heat treating the three-dimensional structure to shape set the three-dimensional structure after the forming step.

EXAMPLE 27

The method of any one or more of Examples 1 through 26, the step of forming further comprising etching or vapor depositing a dome, a barrel, or a combination of the two, or a barrel with a dome tip.

EXAMPLE 28

The method of any one or more of Examples 1 through 27, further comprising laser welding a seam or junction to form a closed shape.

EXAMPLE 29

A method of manufacturing a surgical instrument, the surgical instrument including a catheter and an end effector extending distally from the catheter, the method comprising: forming at least one sensing electrode, ablating electrode, thermocouple, reference electrode, or sensor onto the catheter or the end effector of the surgical instrument by etching or vapor depositing a structure onto a non-conductive material that is layered over a thin film structure to create a single structure.

EXAMPLE 30

The method of Example 29, further comprising heat treating the structure to shape set the structure after the forming step.

EXAMPLE 31

The method of any one or more of Examples 29 through 30, the step of forming further comprising etching or vapor depositing a dome, a barrel, or a combination of the two, or a barrel with a dome tip.

EXAMPLE 32

The method of any one or more of Examples 29 through 31, further comprising laser welding a seam or junction to form a closed shape.

EXAMPLE 33

A surgical instrument comprising: (a) a handle; (b) a catheter extending distally from the handle, a proximal portion of the catheter defining a longitudinal axis; and (c) an end effector extending distally from the catheter, the end effector including at least at least one sensing electrode, ablating electrode, reference electrode, force sensor assembly, position sensor assembly or thermocouple that comprises: (i) a first layer that includes a super elastic material, (ii) a second layer that includes a non-conductive material that contacts the super elastic material, and (iii) a third layer contacting the non-conductive material.

EXAMPLE 34

The surgical instrument of Example 33, the catheter having inner and outer surfaces, the end effector having inner and outer surfaces, the at least one sensing electrode, ablating electrode, reference electrode, force sensor assembly, position sensor assembly or thermocouple being disposed on at least one of the inner surface of the catheter, the inner surface of the end effector, the outer surface of the catheter, or the outer surface of the end effector.

EXAMPLE 35

The surgical instrument of Example 33, the catheter having inner and outer surfaces, the end effector having inner and outer surfaces, the at least one sensing electrode, ablating electrode, reference electrode, force sensor assembly, position sensor assembly or thermocouple being disposed on the inner surface of the catheter or the inner surface of the end effector.

EXAMPLE 36

The surgical instrument of Example 33, the catheter having inner and outer surfaces, the end effector having inner and outer surfaces, the at least one sensing electrode, ablating electrode, reference electrode, force sensor assembly, position sensor assembly or thermocouple being disposed on the outer surface of the catheter or the outer surface of the end effector.

EXAMPLE 37

The surgical instrument of any one or more of 33 through 36, the non-conductive material being selected from the group consisting of polyimide and polyether ether ketone.

EXAMPLE 38

The surgical instrument of any one or more of Examples 33 through 37, the non-conductive material being planar.

EXAMPLE 39

The surgical instrument of any one or more of Examples 33 through 38, the super elastic material comprising a super elastic alloy.

EXAMPLE 40

The surgical instrument of Example 39, the super elastic alloy being nitinol.

EXAMPLE 41

The surgical instrument of Example 39, the super elastic material comprising a shape memory material.

EXAMPLE 42

The surgical instrument of Example 41, the shape memory material comprising a temperature sensitive material, such that the temperature sensitive material is configured to transition from a first shape to a second shape in response to a change in temperature.

EXAMPLE 43

The surgical instrument of any one or more of Examples 33 through 42, further comprising a position sensor, the position sensor being operable to generate a signal indicative of a position of one or both of at least a portion of the catheter or at least a portion of the end effector in a three-dimensional space.

EXAMPLE 44

The surgical instrument of any one or more of Examples 33 through 43, the position sensor assembly being located on a portion of the catheter.

EXAMPLE 45

The surgical instrument of any one or more of Examples 33 through 44, the catheter further including a flexible elongate sheath, the position sensor assembly being located on an inner or outer surface of the flexible elongate sheath of the catheter.

V. Miscellaneous

Any of the instruments described herein may be cleaned and sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, hydrogen peroxide, peracetic acid, and vapor phase sterilization, either with or without a gas plasma, or steam.

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those skilled in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of manufacturing a surgical instrument, the surgical instrument including a sheath and an end effector extending distally from the sheath, the end effector including a cylindraceous nitinol member configured with a dome and a barrel, the method comprising:

forming at least one electrode or thermocouple on the cylindraceous nitinol member of the end effector of the surgical instrument by etching or vapor depositing a first three-dimensional structure of a first electrically-conductive material onto a first non-conductive planar material that is layered over the dome or barrel of the cylindraceous nitinol member, an outer surface of the cylindraceous nitinol member in direct contact with an inner surface of the first non-conductive planar material, an outer surface of the first non-conductive planar material in direct contact with an inner surface of the first electrically-conductive material of the first three-dimensional structure; and forming at least one position sensor or force sensor on the sheath of the surgical instrument by etching or vapor depositing a second three-dimensional structure of a second electrically-conductive material onto a second non-conductive planar material that is layered over a thin film of nitinol, an outer surface of the thin film of nitinol in direct contact with an inner surface of the second non-conductive planar material, an inner surface of the thin film of nitinol in direct contact with an outer surface of the sheath, an outer surface of the second non-conductive planar material in direct contact with an inner surface of the second electrically-conductive material of the second three-dimensional structure.

2. The method of claim 1, further comprising heating to shape set the thin film of nitinol.

3. The method of claim 1, further comprising forming a tab extending proximally from the at least one electrode and providing a circuit disk with circuitry configured to communicate electrically with the at least one electrode via the tab.

4. The method of claim 1, wherein the second electrically-conductive material is magnetic.

5. The method of claim 1, wherein the end effector has inner and outer surfaces and the forming at least one electrode or thermocouple includes forming the at least one electrode or thermocouple on the outer surface of the end effector.

6. The method of claim 1, wherein the end effector has inner and outer surfaces and the forming at least on electrode or thermocouple includes forming the at least one electrode or thermocouple on the inner surface of the end effector.

7. The method of claim 1, wherein the position sensor includes at least one position sensor coil, and the forming the at least one position sensor or force sensor includes etching or vapor depositing the at least one position sensor coil onto the sheath.

8. The method of claim 1, wherein the shaft has inner and outer surfaces and the forming at least one position sensor or force sensor includes forming the at least one position sensor or force sensor on the outer surface of the sheath.

9. The method of claim 1, wherein the shaft has inner and outer surfaces and the forming at least one position sensor or force sensor includes forming the at least one position sensor or force sensor on the inner surface of the sheath.

10. The method of claim 1, wherein the vapor depositing includes physical vapor depositing or chemical vapor depositing.

11. The method of claim 1, the at least one electrode being selected from the group consisting of a sensing electrode, an ablating electrode, and a reference electrode.

12. The method of claim 1, the at least one force sensor further comprising a Rosette strain gauge, vapor depositing the force sensor further comprising vapor depositing the Rosette strain gauge onto the sheath.

13. The method of claim 1, further comprising laser welding a seam or junction to form a closed shape.

14. The method according to claim 1, further comprising:
providing a circuit disk axially aligned with a longitudinal axis of the surgical instrument, the circuit disk configured to communicate electrical signals with the at least one electrode.

15. The method of claim 14, wherein the electrical signals include RF electrical energy.

16. The method of claim 14, wherein the electrical signals include EP mapping signals.

17. The method of claim 1, wherein the thin film of nitinol is configured as a strip.

18. A method of manufacturing an electrophysiology (EP) catheter, the EP catheter including a catheter sheath and an end effector extending distally from the catheter sheath, the end effector including a cylindraceous nitinol member the method comprising:
forming at least one electrode or thermocouple on the cylindraceous nitinol member of the end effector by etching or vapor depositing a first three-dimensional structure of a first electrically-conductive material onto a first non-conductive planar material that is layered over the cylindraceous nitinol member, an outer surface of the cylindraceous nitinol member in direct contact with an inner surface of the first non-conductive planar material, an outer surface of the first non-conductive planar material in direct contact with an inner surface of the first electrically-conductive material of the first three-dimensional structure;
forming together as at least one single unitary structure one respective position sensor coil and one respective force sensor on the catheter sheath by etching or vapor depositing a second three-dimensional structure of a second electrically-conductive material onto a second non-conductive planar material that is layered over a thin film of nitinol, an outer surface of the thin film of nitinol in direct contact with an inner surface of the second non-conductive planar material, an inner surface of the thin film of nitinol in direct contact with an outer surface of the catheter sheath, an outer surface of the second non-conductive planar material in direct contact with an inner surface of the second electrically-conductive material of the second three-dimensional structure.

19. The method of claim 18, further comprising:
heating treating to shape set the thin film of nitinol; and
laser welding a seam or junction structure leaving irrigation openings open.

* * * * *